United States Patent
Ochs et al.

(10) Patent No.: US 8,532,765 B2
(45) Date of Patent: Sep. 10, 2013

(54) CPR COACHING DEVICE WITH REDUCED SENSITIVITY TO MOTION

(75) Inventors: Dennis Ochs, Bellevue, WA (US); Daniel Powers, Issaquah, WA (US)

(73) Assignee: Koninklijke Philips N.V., Eindhoven (NL)

(*) Notice: Subject to any disclaimer, the term of this patent is extended or adjusted under 35 U.S.C. 154(b) by 931 days.

(21) Appl. No.: 12/514,474

(22) PCT Filed: Nov. 6, 2007

(86) PCT No.: PCT/IB2007/054497
§ 371 (c)(1),
(2), (4) Date: May 12, 2009

(87) PCT Pub. No.: WO2008/059394
PCT Pub. Date: May 22, 2008

(65) Prior Publication Data
US 2010/0049266 A1    Feb. 25, 2010

Related U.S. Application Data

(60) Provisional application No. 60/865,666, filed on Nov. 14, 2006.

(51) Int. Cl.
*A61N 1/00*    (2006.01)
(52) U.S. Cl.
USPC .......................................................... 607/6
(58) Field of Classification Search
USPC .......................................................... 607/6
See application file for complete search history.

(56) References Cited

U.S. PATENT DOCUMENTS

| | | | |
|---|---|---|---|
| 6,178,357 B1 * | 1/2001 | Gliner et al. | 607/142 |
| 6,287,328 B1 | 9/2001 | Snyder et al. | |
| 2004/0082888 A1 | 4/2004 | Palazzolo et al. | |
| 2004/0210171 A1 * | 10/2004 | Palazzolo et al. | 601/41 |
| 2004/0267325 A1 * | 12/2004 | Geheb et al. | 607/5 |
| 2006/0015044 A1 * | 1/2006 | Stavland et al. | 601/41 |
| 2006/0023650 A1 * | 2/2006 | Dominique et al. | 370/310 |
| 2006/0116724 A1 * | 6/2006 | Snyder | 607/5 |
| 2006/0247560 A1 * | 11/2006 | Halperin et al. | 601/41 |
| 2006/0270952 A1 * | 11/2006 | Freeman et al. | 601/41 |

* cited by examiner

Primary Examiner — Niketa Patel
Assistant Examiner — Minh Duc Pham

(57) ABSTRACT

A CPR coaching device is designed for placement on the chest of a patient during CPR. Chest compressions are delivered to the patient by a rescuer by pressing on the device. A force sensor and an accelerometer are located in the device and are responsive to the chest compressions. When the patient's body is stationary there will be a high correlation of a depth signal produced by doubly integrating the acceleration signal of the accelerometer and the force signal, and the depth signal is deemed reliable. When the patient's body is subject to motion such as by the motion of a vehicle transporting the patient, there will be a low correlation of the depth and force signals, with the force signal being relatively immune to this motion. In such cases, the force signal is used in association with the previously determined relationship between depth and force in the absence of motion to produce an indication of chest compression depth.

20 Claims, 5 Drawing Sheets

CPR COACHING DEVICE WITH REDUCED SENSITIVITY TO MOTION

The invention relates generally to medical devices, and more particularly, to cardio-pulmonary resuscitation (CPR) coaching and training devices.

Cardiac arrest is a life-threatening medical condition in which the patient's heart fails to provide blood flow to support life. CPR can be administered to a patient experiencing cardiac arrest to cause blood to flow in the patient. A rescuer administers CPR by compressing the patient's chest interspersed with blowing into the patient's mouth to fill the lungs with oxygen. CPR can be combined with other forms of therapy as well, such as defibrillation therapy. As is known, during cardiac arrest, the electrical activity of the heart may be disorganized (ventricular fibrillation, "VF"), too rapid (ventricular tachycardia, "VT"), absent (asystole), or organized at a normal or a slow heart rate without producing blood flow (pulseless electrical activity). A defibrillation shock delivered to a patient suffering from VF or VT can stop the unsynchronized or rapid electrical activity and allow a normal sinus rhythm to return. Between the times defibrillation shocks are delivered to a patient, CPR is administered to promote blood flow.

Studies have suggested that a patient's survival prospects can be improved by the administration of high-quality CPR. The quality of the CPR is directly related to the quality of the chest compressions, a part of which is determined by compression depth. That is, good chest compressions are generally those which depress the chest of an adult by four centimeters and about two and a half centimeters for a child. There are many guidelines known in the art that set out desired compression depths for CPR. See, for instance, Guidelines 2000 for Cardiopulmonary Resuscitation and Emergency Cardiovascular Care, 102 Circulation Supp. I (2000). Learning to administer chest compressions of sufficient depth is traditionally part of CPR training. For example, in practice situations involving manikins, compression depth is commonly measured and the information fed back to the participant. It is assumed that by practicing chest compressions on a manikin, the participant will be capable of repeating the same movement pattern on real human patients. However, studies have shown that the ability to repeat the movement pattern of administering chest compressions is poor even immediately after being trained, and not surprisingly, becomes worse over time. Additionally, since human anatomy varies from person to person, patients have differing degrees of resistance to chest compressions and require different levels of force to sufficiently compress the chest. As a result, learning to administer chest compressions of uniform, correct compression depth through CPR training on a manikin is difficult to achieve. It would be desirable to have a device that assists a CPR rescuer by guiding the rescuer in the proper depth of chest compressions as CPR is administered.

Various devices have been proposed to assist a rescuer in properly applying CPR. For example, U.S. Pat. No. 5,496,257 (Kelley) shows a device that uses a pressure sensor to monitor compression forces and timing. U.S. Pat. No. 6,125,299 (Groenke et al.) shows a device that uses a force sensor to measure the compression force applied to a patient's chest. However, these devices only measure the force applied to the chest and do not measure the actual depth of compressions. A given force can compress the chests of different patients by different amounts, so measuring only force will not provide sufficient or consistent feedback to the rescuer. In addition, force-based measurements may also be inaccurate because of intra-patient variation in thoracic morphology and compliance (stiffness).

CPR devices that use only accelerometers to measure depth of compressions may not fully or accurately account for errors in the measured acceleration; nor may they account for drift in the starting points of compressions. Furthermore, the integration process necessary to derive the depth of compressions greatly compounds any errors in the measured acceleration. It is important to correct for errors in the measured acceleration since the total depth of compressions should be within the relatively narrow range of 1.5 inches to 2.0 inches. U.S. Publication 2001/0047140 (Freeman) shows a device that uses an accelerometer as a compression sensor and mentions gauging chest depth with the accelerometer. However, Freeman provides no method to account for the errors inherent in using an accelerometer alone. Thus this technique may be subject to the aforementioned inaccuracies. See also U.S. Pat. No. 6,306,107 (Myklebust et al.) which describes a device which uses a pressure pad containing an accelerometer and a force activated switch to determine the depth of depressions.

The use of an accelerometer to measure chest compression depth during CPR is also complicated by at least two sources of error: signal error and external acceleration error. Signal error comprises errors in the measured acceleration due to electronic noise, the shaking of wires or cables, errors inherent in the accelerometer, and other sources of noise in the acceleration itself. External acceleration error comprises errors introduced by accelerations applied to the patient and/or the accelerometer other than accelerations caused by CPR. For example, if the patient is being transported in an ambulance and a rescuer is applying manual CPR with a compression monitor, then the accelerometer will measure accelerations caused by road vibrations as well as accelerations caused by CPR. If the ambulance bounces over a rough road, a large spike may appear in the compression data. The accelerometer, by itself, cannot distinguish between the accelerations caused by road noise and the accelerations caused by compressions. The accelerometer measures combined acceleration and not just the accelerations caused by compressions. Accordingly, the compression monitor will report a displacement value different from the actual chest displacement. Prior art attempts to overcome this problem have included the use of a second accelerometer which is placed beneath the victim during CPR. The second accelerometer will thus respond to the common mode motion of the vehicle but will not respond to the compression strokes on the chest of the patient. Subtracting the common mode signal of the second accelerometer from the signal of the compressed chest accelerometer will remove the common mode vehicle motion from the measurement. However, this approach requires another accelerometer and its connections and processing, further complicating the rescue process for the rescuer. It is desirable to be able to account for such external error factors without the need for additional wires and hardware.

In accordance with the principles of the present invention, a depth based CPR coaching system and method are provided which are accurate even in a moving vehicle. The inventive system and method employ an accelerometer responsive to chest compressions that produces an acceleration signal which, when doubly integrated, produces a measurement of chest compression depth. A force sensor is also responsive to the chest compressions and produces a signal which is a measure of the force of compression. The two signals are correlated or compared to assess the reliability of the depth measurement. While the depth signal may be affected by the motion of a moving vehicle, the force signal may not be. A sustained correlation of depth and force over a number of compression strokes indicates a reliable depth measurement. When the depth signal becomes unreliable, the force signal may be used to indicate compression depth using the previously determined relationship between force and depth. This information may be used to provide feedback to a rescuer as to the correctness of the CPR compressions.

IN THE DRAWINGS

Figure 1:
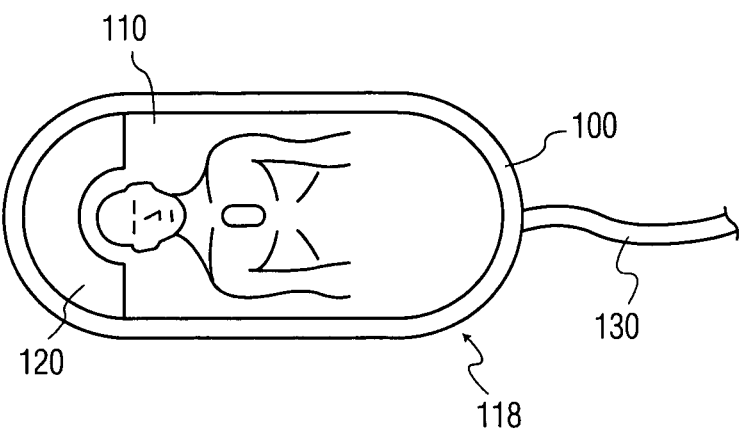
FIG. 1 is a diagram of a CPR coaching device according to an embodiment of the present invention.

FIG. 1 illustrates a CPR coaching device 100 constructed in accordance with the principles of the present invention. The CPR coaching device 100 is operable to coach a rescuer in administering CPR to a patient, such as by providing feedback on whether chest compressions are of sufficient depth and whether the pace of the chest compressions is adequate. The signals provided by the CPR coaching device are relatively immune to common mode motion such as the bouncing of an ambulance on rough roads.

An upper portion 120 of a housing 118 of the CPR coaching device 100 is shown in FIG. 1. An illustration 110 depicting a patient's torso is included on the upper portion 120 of the CPR coaching device 100 to illustrate the proper position and orientation of the CPR coaching device 100 on the patient during CPR. In this position the lower portion of the device 100 opposite the upper portion 120 is in contact with the torso of the patient. The CPR coaching device may be attached to the patient by an adhesive layer present on a lower portion 124 of the housing 118 of the CPR coaching device 100. The lower portion 124 is configured to be placed against the patient's chest and does not need to have any electrodes that are electrically coupled to the patient. The lower portion 124 can be made from a material that electrically insulates the CPR coaching device 100 from the patient. In various embodiments of the invention the adhesive layer on the patient contact surface of portion 124 may be formed from a material that also provides an acoustic coupling medium, such as hydrogel. This feature will enable good detection of patient physiological information by an acoustic or ultrasound sensor incorporated into the device 100 as described in U.S. patent application 60/821,371 filed Aug. 3, 2006, of which one of us is a co-inventor. A cable 130 is used to couple the physiological and coaching information produced by the coaching device to another medical device, such as a coaching instruction enunciator or a defibrillator, to which the CPR coaching device 100 is attached.

Figure 2:
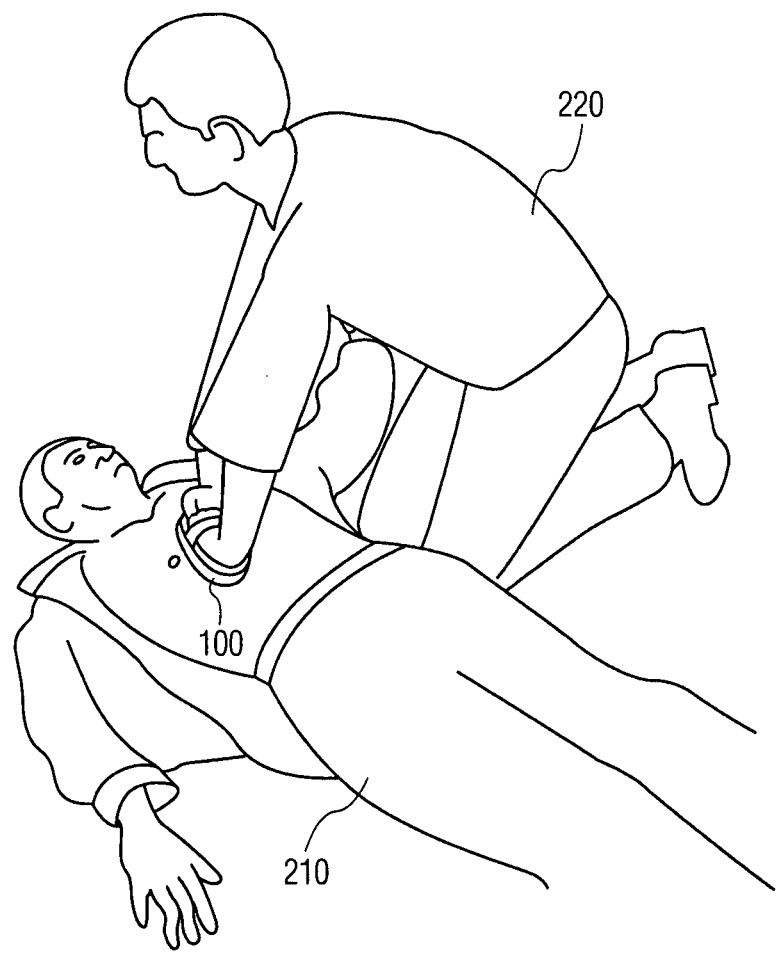
FIG. 2 illustrates a rescuer using a CPR coaching device according to an embodiment of the present invention for administering CPR to a patient.

As shown in FIG. 2, with the CPR coaching device 100 positioned on the sternum of a patient 210, a rescuer 220 prepares to apply chest compressions in a conventional manner using two hands with one placed over the other. Instead of placing the hands directly on the patient 210, however, the rescuer's hands are placed on the CPR coaching device 100 and chest compressions are applied to the patient 210 via the CPR coaching device 100. Chest compressions are administered by the rescuer 220 as prescribed by conventional CPR protocols. As will be described in more detail below, the CPR coaching device 100 measures the depth of each compression with an accelerometer and the force of each compression with a force sensor. These two signals are correlated to provide a compression depth signal which is corrected for external motion such as the motion of a moving vehicle.

Figure 3:
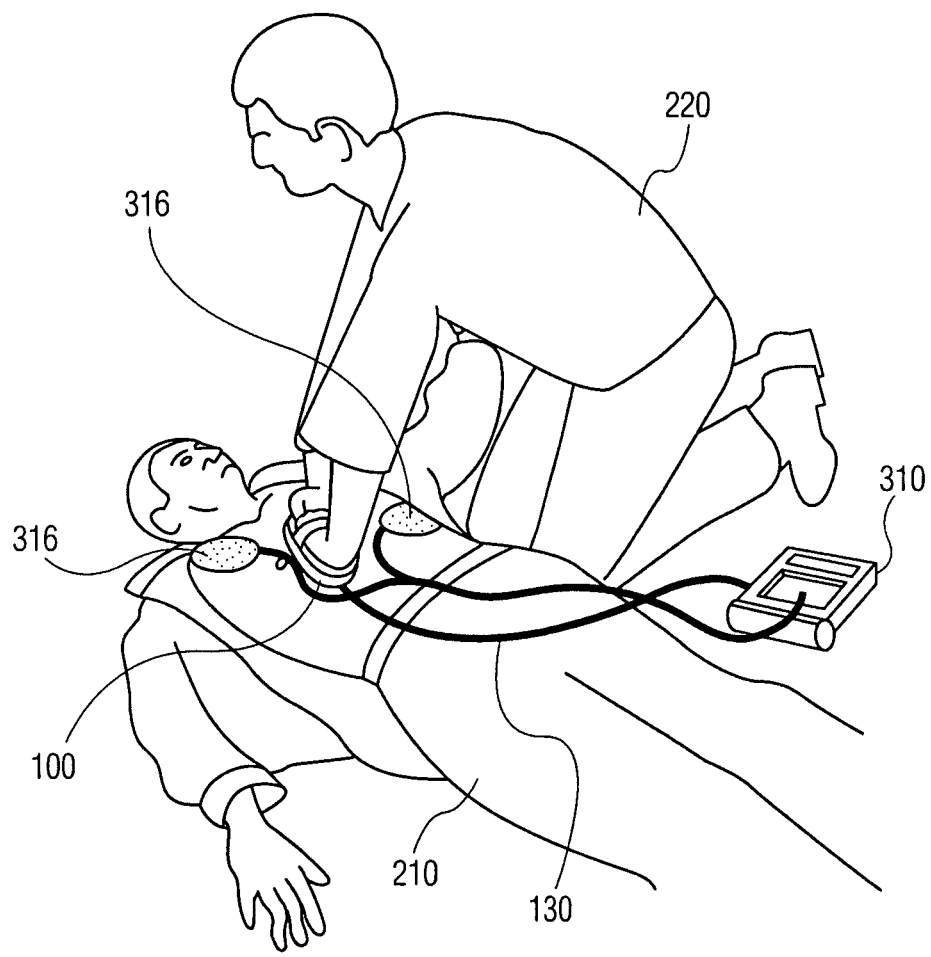
FIG. 3 illustrates a rescuer using a CPR coaching device and defibrillator according to another embodiment of the present invention.

In the example of FIG. 3, a defibrillator 310 is attached to the patient 210 by electrodes 316. The defibrillator 310, as known, can be used to deliver defibrillating shocks to the patient 210 suffering from cardiac arrest. More specifically, the defibrillator can deliver a high-voltage impulse to the heart in order to restore normal rhythm and contractile function in patients who are experiencing arrhythmia such as VF or VT that is not accompanied by spontaneous circulation. There are several classes of defibrillators, including manual defibrillators, implantable defibrillators, and automatic external defibrillators (AEDs). AEDs differ from manual defibrillators in that AEDs can automatically analyze the electrocardiogram (ECG) rhythm to determine if defibrillation is necessary. In most AED designs, the user is prompted to press a shock button to deliver the defibrillation shock to the patient when a shock is advised by the AED.

The electrodes 316 are applied across the chest of the patient 210 by the rescuer 220 in order to acquire an ECG signal from the patient's heart. The defibrillator 310 then analyzes the ECG signal for signs of arrhythmia. If VF is detected, the defibrillator 310 signals the rescuer 220 that a shock is advised. After detecting VF or other shockable rhythm, the rescuer 220 then presses a shock button on the defibrillator 310 to deliver defibrillation pulse to resuscitate the patient 210. The CPR coaching device 100 is coupled to the defibrillator 310 by the electrical cable 130 to provide the defibrillator 310 with physiological information obtained by sensors contained in the CPR coaching device 100 if present. The electrical cable provides power for electronic components in the coaching device 100 and couples compression depth signals to the defibrillator 310 where they can be used to issue audible CPR instructions through the loudspeaker of the defibrillator 310.

Figure 4:
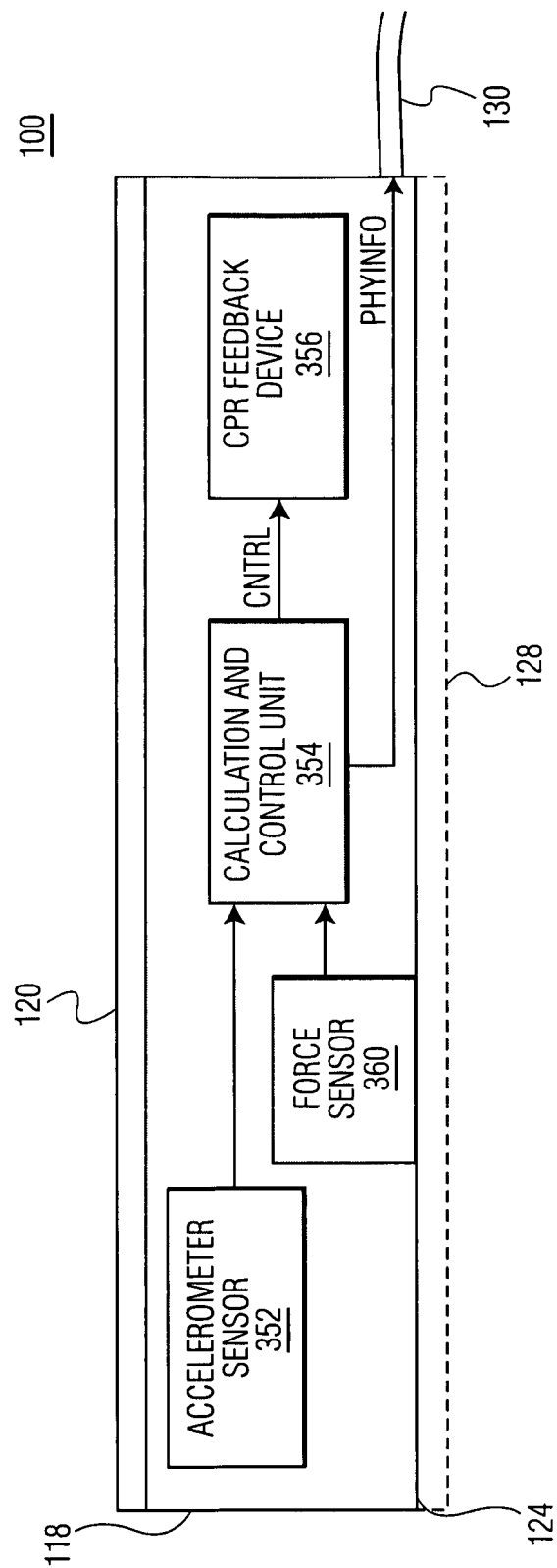
FIG. 4 is a block diagram of components included in a CPR coaching device constructed in accordance with the principles of the present invention.

FIG. 4 is a block diagram of various components included in one example of the CPR coaching device 100 according to the present invention. A CPR compression sensor 352 included in the CPR coaching device 100 senses characteristics related to chest compressions being applied to the patient 210. In this example the CPR compression sensor 352 is an accelerometer that is operable to detect and measure acceleration of the CPR coaching device 100 during administration of chest compressions. As previously described, the measured acceleration is used to gauge the sufficiency of the depth of the chest compressions applied by the rescuer 220. The accelerometer sensor 352 generates output signals in response to sensing the chest compression which are coupled to a calculation and control unit 354 for comparison or correlation with a force signal produced by a force sensor 360 in the device 100. Both the accelerometer sensor and the force sensor 360 are subject to the compression strokes of the rescuer so that both devices produce output signals for processing in response to each chest compression.

A calculation and control unit 354 is coupled to receive the output signals from both the accelerometer sensor 352 and the force sensor 360. The calculation and control unit 354 includes processing and calculation circuitry known in the art that is operable to determine the depth of the chest compressions from the signals produced by the accelerometer sensor such as is described in the aforementioned Myklebust et al. patent which is incorporated herein by reference. As described therein, the calculation and control unit 354 is programmed to perform double-integration of the acceleration signal to calculate a displacement (depth of compression) of the CPR coaching device 100. The calculated depth of displacement can be compared to a standard for compression depth, e.g., 1.5-2.0 inches, to determine if the chest compressions are of sufficient depth. If the chest compressions are found to be outside the proper depth range, a PHYINFO signal is coupled to a CPR feedback device 356 by means of the cable 130, which uses the signal to issue an audible or visual instruction to the rescuer to, for instance, "PRESS DEEPER" or "PRESS SHALLOWER." In other embodiments of the invention, the calculation and control unit 354 is further operable to determine a pace (rate) of the chest compressions being administered, and a pacing signal is sent to the CPR feedback device for audible or visual presentation to the rescuer. In various embodiments of the invention, the CPR feedback device 356 is a visual display device for providing visual feedback to the rescuer 220. In other embodiments the CPR feedback device is alternatively or additionally an audio device for providing audible feedback to the rescuer 220. The visual and/or audible feedback is provided to coach the rescuer 220 on whether the depth of the chest compressions is sufficient, for example, too deep, not deep enough, or within a range of acceptable depth. Where the calculation and control unit 354 is further operable to determine the pace of the chest compressions, the PHYINFO signals include signals to control the CPR feedback device 356 to further coach the rescuer 220 on the pace of the chest compressions, such as, coaching the rescuer to administer the chest compressions faster or slower.

In accordance with the principles of the present invention the calculation and control unit 354 also compares or correlates the force signal from the force sensor with the acceleration or depth signal received from the accelerometer sensor or produced in response thereto. Since both sensors are responsive to the compression strokes of the rescuer the two signals will be time concurrent. The signals will also exhibit a relatively constant relation to each other in the absence of external motional effects. That is, a series of compressions of considerable depth will be accompanied by force signals of a relatively high magnitude. When shallow compressions are applied, the depth signal will be low and the force signal will be of a relatively lower magnitude. When the rescuer is applying relatively consistent compressions the sequence of acceleration signals will be accompanied by relatively consistent force signals. Thus there is developed a reliable relationship of acceleration (depth) and force in the absence of external motional effects. The relationship between acceleration (depth) and force under these high correlation conditions is identified and stored by the calculation and control unit for possible subsequent use.

But in the presence of external motional effects such as the bouncing of a moving ambulance, the comparison or correlation of these signals will deteriorate. The acceleration signal will reflect the up and down motion of the patient and vehicle. But the force signal will remain substantially constant as the vehicle supporting the patient and the rescuer will be moving up and down in unison. Thus, while the acceleration signal will be affected by this external motion, the force signal is substantially unaffected. This different relation between the acceleration and force signals will be reflected in the comparison or correlation of the two signals, which will be poorer than in the stationary case. A lower degree of correlation thus indicates that the depth measurement produced from the acceleration signal may not be reliable. However the force signal is also not to be used since, as mentioned above, the relationship between force and depth varies from one individual to another. In accordance with a further aspect of the present invention, in an embodiment where the depth/force relationship was previously identified under high correlation conditions and saved, that information may be used such as in a lookup table form by producing a depth output signal from the saved information that relates to the force signal currently produced. The previously stored depth/force relation information is used to produce a depth estimate for CPR coaching until a high correlation factor indicates a return to a depth (acceleration) signal that is reliable. In summary, when the depth measurement is determined to be unaffected by external motion, the depth measurement alone is used to provide CPR feedback. But in the situation where the depth measurement is found to be contaminated by external motion, the force signal is used at least indirectly to estimate depth by translating the force signal to an estimated depth using the previously identified relationship between force and depth under uncontaminated conditions. In other implementations a combination or weighted average of both force and depth can be used, with the weighting dependent upon correlation of the signals or other weighting factors.

As previously mentioned, the CPR feedback device 356 can be contained within another medical device such as a defibrillator or AED or a CPR coaching enunciator. The CPR feedback device may also or alternatively be located in the CPR coaching device 100 itself, which may avoid the need for cable 130 and external equipment. Likewise, the calculation and control unit 354 can be located in the coaching device 100 as shown in FIG. 4, or may be located in a separate housing or medical device at the remote end of cable 130. Wireless configurations are also possible.

Figure 5:
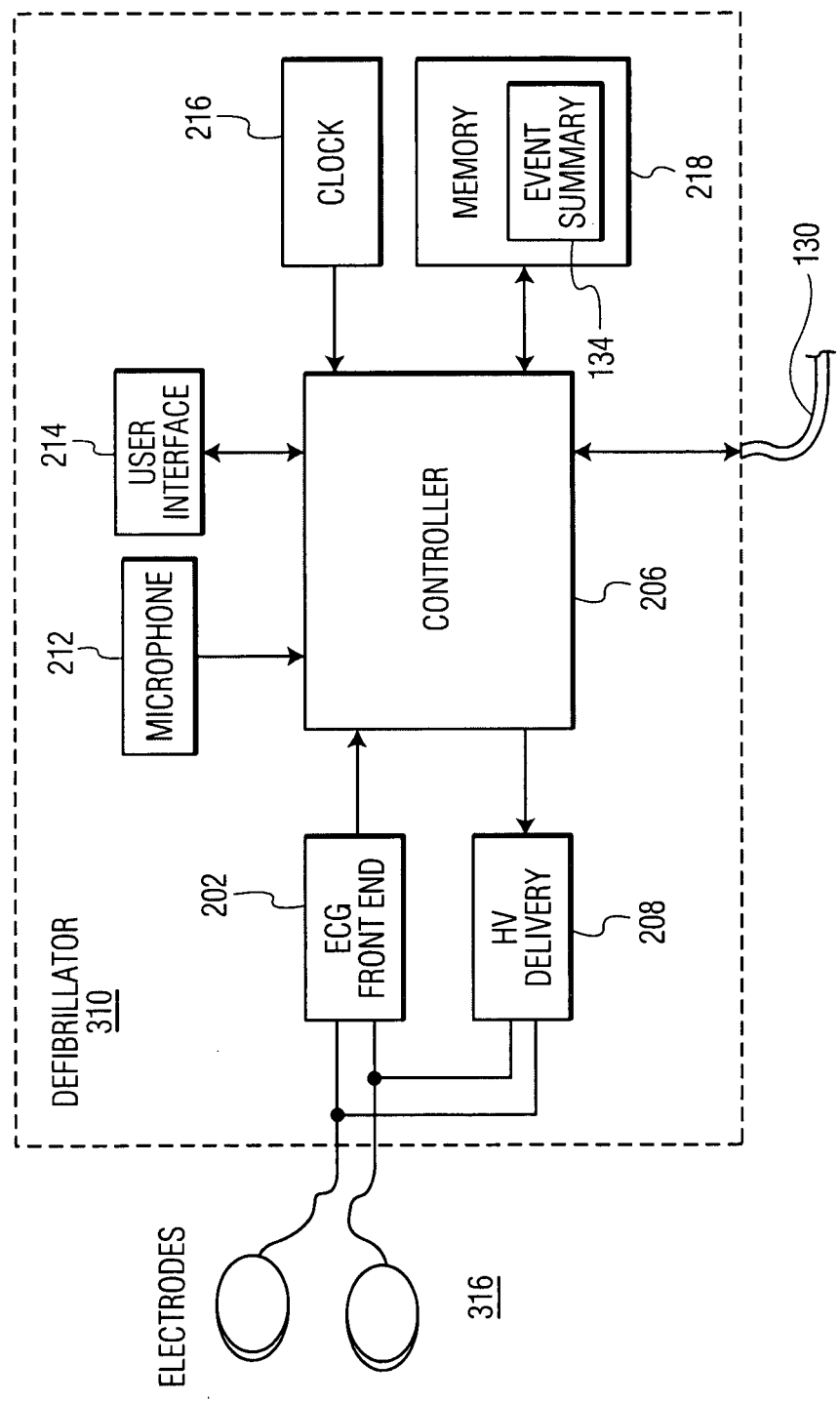
FIG. 5 is a block diagram of a defibrillator to which a CPR coaching device of the present invention is coupled for combined defibrillation and CPR coaching.

FIG. 5 illustrates various components included in the defibrillator 310 (FIG. 3) to which the CPR coaching device 100 is coupled through cable 130. The defibrillator 310 is designed for small physical size, light weight, and relatively simple user interface capable of being operated by personnel without high training levels or who otherwise would use the defibrillator 310 only infrequently. In contrast, a paramedic or clinical (manual) defibrillator of the type generally carried by an emergency medical service (EMS) responder tends to be larger, heavier, and have a more complex user interface capable of supporting a larger number of manual monitoring and analysis functions and protocol settings.

An ECG front end circuit 202 is connected to the electrodes 316 that are connected across the chest of the patient 210. The ECG front end circuit 202 operates to amplify, buffer, filter and digitize an electrical ECG signal generated by the patient's heart to produce a stream of digitized ECG samples. The digitized ECG samples are provided to a controller 206 that performs an analysis to detect VF, shockable VT or other shockable rhythm. If a shockable rhythm is detected, the controller 206 sends a signal to HV (high voltage) delivery circuit 208 to charge a high voltage capacitor of circuit 208 in preparation for delivering a shock, and a shock button on a user interface 214 is activated to begin flashing. The rescuer 220 is then advised by an audible instruction to keep away from the patient 210 ("hands off" instruction). When the rescuer 220 presses the shock button on the user interface 214 a defibrillation shock is delivered from the HV delivery circuit 208 to the patient 210 through the electrodes 316.

The controller 206 is coupled to further receive input from a microphone 212 to produce a voice strip. The analog audio signal from the microphone 212 is preferably digitized to produce a stream of digitized audio samples which may be stored as part of an event summary 134 in a memory 218. The user interface 214 may consist of a display, an audio speaker, and control buttons such as an on-off button and a shock button for providing user control as well as visual and audible prompts. A user interface of the present invention may also include one or more control buttons for selecting a rescue protocol stored in memory 218 to be carried out during a rescue. A clock 216 provides real-time or elapsed time clock data to the controller 206 for time-stamping information contained in the event summary 134. The memory 218, implemented either as on-board RAM, a removable memory card, or a combination of different memory technologies, operates to store the event summary 134 digitally as it is compiled during the treatment of the patient 210. The event summary 134 may include the streams of digitized ECG, audio samples, time and energy of shocks delivered, and other event data as previously described.

The controller 206 is further coupled to the CPR coaching device 100 through the cable 130, through which the PHYINFO signals are received by the controller 206. The controller 206 receives the PHYINFO signals from the CPR coaching device 100 and prepares the signals for use by the controller 206. For example, as previously described, the physiological information obtained by the CPR coaching device 100 can be used by the defibrillator 310 in determining an appropriate resuscitation protocol. For example, prior to delivering a shock to the patient, the controller 206 is operable to determine whether a patient pulse is present based on information sensed by a physiological sensor in embodiments where a pulse sensor is contained in the device 100. Pulse information along with ECG information can be considered by the controller 206 in determining an appropriate resuscitation protocol. The CPR signals produced in response to the accelerometer sensor 352 and/or the force sensor 360 can be used by the controller to adjust the CPR protocol for example by giving audible and/or visual instructions to press faster or slower or deeper or shallower.

Figure 6:
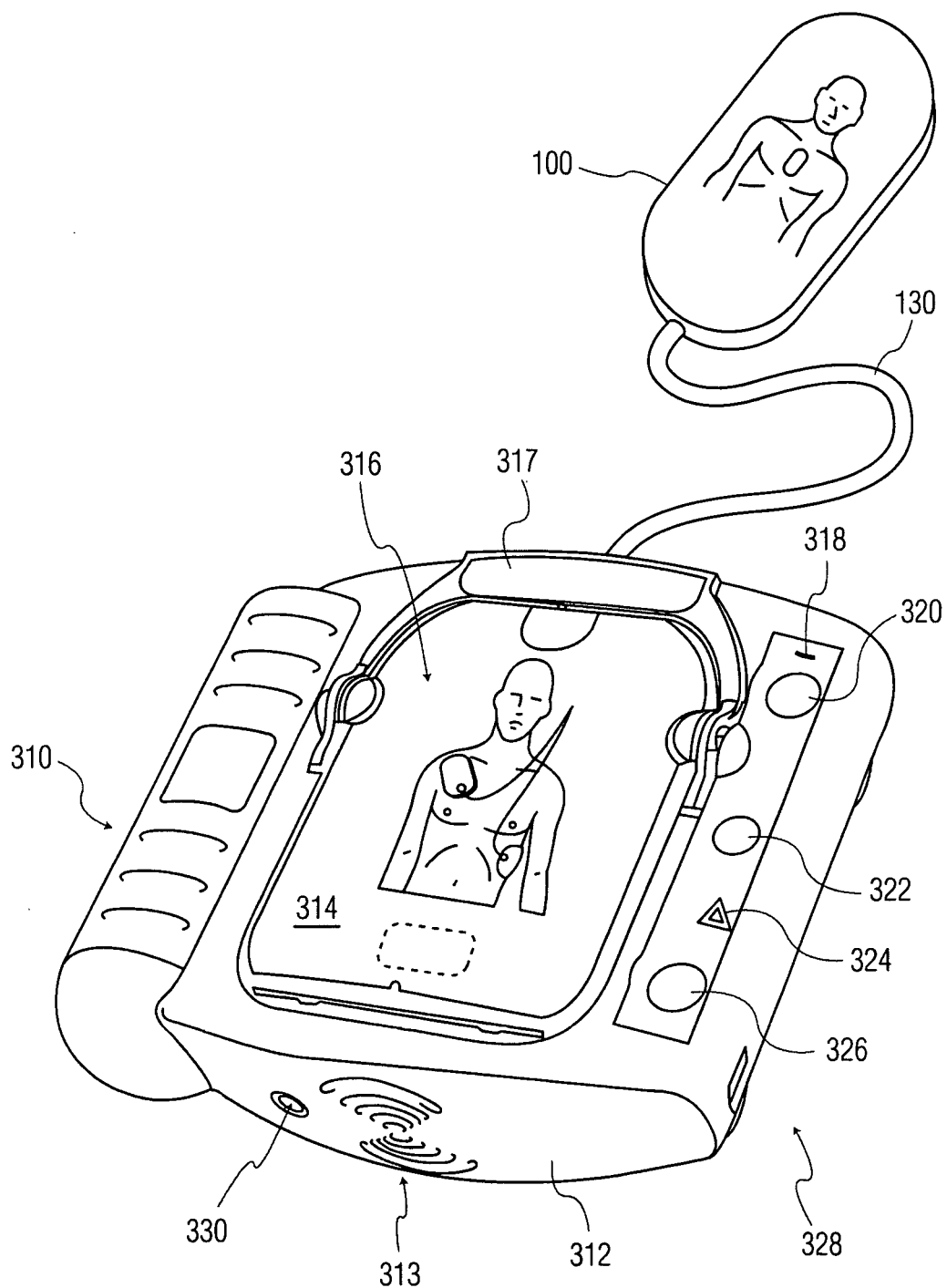
FIG. 6 is an illustration of a CPR coaching device coupled to a defibrillator according to another embodiment of the present invention.

FIG. 6 illustrates the CPR coaching device 100 coupled through cable 130 to the defibrillator 310. The defibrillator 310 represents a semi-automatic external defibrillator (AED). However, other types of defibrillators can be used as well. The AED 310 is housed in a rugged polymeric case 312 which protects the electronic circuitry inside the case, which was previously described with reference to FIG. 5, and also protects the rescuer 220 from shocks. Attached to the case 312 by electrical leads are a pair of electrodes 316. The electrodes 316 are housed in a cartridge 314 located in a recess on the top side of the AED 310. The electrode pads are accessed for use by pulling up on a handle 317 which allows removal of a plastic cover over the electrodes 316. The user interface is on the right side of the AED 310. A small ready light 318 informs the rescuer 220 of the readiness of the AED 310. In this embodiment the ready light blinks after the AED 310 has been properly set up and is ready for use. The ready light is on constantly when the AED 310 is in use, and the ready light is off or flashes in an alerting color when the AED 310 needs attention.

Below the ready light is an on/off button 320. The on/off button is pressed to turn on the AED 310 for use. To turn off the AED 310 the rescuer 220 holds the on/off button down for one second or more. An information button 322 flashes when information is available for the rescuer 220. The rescuer 220 depresses the information button to access the available information, which is then presented as an audible message. A caution light 324 blinks when the AED 310 is acquiring heartbeat information from the patient 210 and lights continuously when a shock is advised, alerting the rescuer 220 and others that no one should be touching the patient 210 during these times. A shock button 326 is depressed to deliver a shock after the AED 310 informs the rescuer 220 that a shock is advised. An infrared port 328 on the side of the AED 310 is used to transfer data between the AED 310 and a computer. This data port finds used after the patient 210 has been rescued and a physician desires to have the AED 310 event data downloaded to his or her computer for detailed analysis. A speaker 313 provides voice instructions to the rescuer 220 to guide the rescuer 220 through the use of the AED 310 to treat the patient 210. A beeper 330 is provided which "chirps" when the AED 310 needs attention such as electrode pad replacement or a new battery. The beeper can also be used as a metronome tone which chirps at the appropriate rate of CPR chest compressions.

In another embodiment the CPR coaching device includes ECG electrodes on the body-contacting surface of the device for the sensing of the patient's ECG signal. The ECG signal detected by the CPR coaching device is coupled to the ECG front end circuit 202 for processing. In one implementation the CPR coaching device of this embodiment is applied to the patient's chest before the usual defibrillator electrodes are unwrapped and applied. The ECG sensor on the coaching device can thereby give the defibrillator a "quick look" at the patient's ECG waveform. For instance, if the ECG signals is sensed and processed to determine that the patient exhibits a viable ECG signal, the defibrillator can alert the rescuer that defibrillation is not advised for the patient. The rescuer does not need to unwrap and apply the defibrillation electrodes to the patient and another form of therapy may be recommended by the defibrillator such as CPR.

What is claimed is:

1. A CPR therapy system comprising:
a CPR coaching device operable to coach a rescuer in administering CPR to a patient, the CPR coaching device having a housing that includes an upper portion and a lower portion, the upper portion configured for placement of at least one of the rescuer's hands for delivery of chest compression force to the patient and the lower portion configured to be placed against the patient's chest,
the CPR coaching device further including an accelerometer sensor responsive to the chest compression force which produces an acceleration signal, a force sensor responsive to the chest compression force which produces a force signal, and
wherein the CPR therapy system further includes a processor responsive to the acceleration signal and the force signal, wherein the processor compares the two signals and reduces the effect of external motion not caused by the chest compression force on the CPR coaching device and the patient,
wherein the processor is further responsive to the acceleration signal to doubly integrate the acceleration signal to produce a measure of chest compression depth,
wherein the processor is operable to assess the reliability of the measure of chest compression depth,
wherein the comparison further comprises correlation of the measure of chest compression depth and the force signal,
wherein, when the correlation of the depth measure and the force signal is relatively low, the depth measure is assessed as being unreliable and a previously determined relationship between force and depth is utilized as a measure of chest compression depth.

2. The CPR therapy system of claim 1, wherein the system is further operable to indicate depth as a combination of the force signal and the acceleration signal when the reliability of the acceleration signal alone is low.

3. The CPR therapy system of claim 1, wherein the comparison further comprises correlation of the acceleration signal and the force signal.

4. The CPR therapy system of claim 1, wherein, when the correlation of the depth measure and the force signal is relatively high, the depth measure is assessed as being reliable.

5. The CPR therapy system of claim 1, further comprising an output device responsive to the processor which acts to produce coaching instructions.

6. The CPR therapy system of claim 5, wherein the output device is a loudspeaker and the coaching instructions are produced audibly.

7. The CPR therapy system of claim 5, wherein the output device is a display and the coaching instructions are visibly displayed.

8. The CPR therapy system of claim 5, further comprising a defibrillator having a defibrillator housing and coupled to the CPR coaching device,
wherein the output device is located in the defibrillator housing.

9. The CPR therapy system of claim 8, wherein the processor is located in the defibrillator housing.

10. A CPR therapy system comprising:
a chest compression housing that includes an upper portion and a lower portion, the upper portion configured for placement of at least one of the rescuer's hands for delivery of chest compression force to the patient and the lower portion configured to be placed against the patient's chest;
an accelerometer sensor, located in the housing and responsive to chest compression force, which acts to produce an acceleration signal which includes a component due to the movement of the patient's chest and may include a component due to the movement of the entire patient that is not caused by the chest compression force;
a force sensor, located in the housing and responsive to chest compression force, which acts to produce a force signal;
a data storage device which acts to store the relationship between the depth signal and the force signal when there is a relatively high correlation of the depth signal and the force signal; and
a processor responsive to the acceleration signal and the force signal which utilizes the two signals to produce a depth signal and to detect the presence of a signal component due to the movement of the entire patient that is not caused by the chest compression force.

11. The CPR therapy system of claim 10, wherein the processor doubly integrates the acceleration signal to produce the depth signal.

12. The CPR therapy system of claim 11, wherein the processor performs a correlation of the depth signal and the force signal to detect the presence of a signal component due to the movement of the entire patient.

13. The CPR therapy system of claim 10, wherein the stored relationship between the depth signal and the force signal is utilized in association with the force signal for the production of a corrected depth signal when there is a relatively low correlation of the depth signal and the force signal.

14. A CPR coaching device operable to coach a rescuer in administering CPR to a patient, comprising:
a housing that includes an upper portion and a lower portion, the upper portion configured for placement of at least one of the rescuer's hands for delivery of chest compression force to the patient and the lower portion configured to be placed against the patient's chest;
an accelerometer sensor responsive to the chest compression force which produces an acceleration signal;
a force sensor responsive to the chest compression force which produces a force signal;
a data storage device; and
a processor that
compares the acceleration signal and the force signal and determines whether a measure of chest compression depth produced from the acceleration signal is reliable or unreliable,
uses the measure of chest compression depth produced from the acceleration signal if the measure is reliable,
stores in the data storage device a relationship between the force signal and the measure of chest compression depth produced from the acceleration signal if the measure is reliable, and
produces an estimated chest compression depth based upon the relationship if the measure is unreliable.

15. A CPR therapy system comprising:
a CPR coaching device operable to coach a rescuer in administering CPR to a patient, the CPR coaching device having a housing that includes an upper portion and a lower portion, the upper portion configured for placement of at least one of the rescuer's hands for delivery of chest compression force to the patient and the lower portion configured to be placed against the patient's chest,
the CPR coaching device further including an accelerometer sensor responsive to the chest compression force which produces an acceleration signal, a force sensor responsive to the chest compression force which produces a force signal, and
wherein the CPR therapy system further includes a processor responsive to the acceleration signal and the force signal, wherein the processor compares the two signals and reduces the effect of external motion not caused by the chest compression force on the CPR coaching device and the patient,
wherein the processor is further responsive to the acceleration signal to doubly integrate the acceleration signal to produce a measure of chest compression depth,
wherein the processor is operable to assess the reliability of the measure of chest compression depth; and
a data storage device which is operable to store a relationship between the force signal and depth when the depth measurement is assessed as being reliable,
wherein the system is operable to utilize the stored relationship when the depth measurement is assessed as being unreliable.

16. The CPR therapy system of claim 15, further comprising an output device responsive to the processor which acts to produce coaching instructions.

17. The CPR therapy system of claim 16, wherein the output device is a loudspeaker and the coaching instructions are produced audibly.

18. The CPR therapy system of claim 16, wherein the output device is a display and the coaching instructions are visibly displayed.

19. The CPR therapy system of claim 16, further comprising a defibrillator having a defibrillator housing and coupled to the CPR coaching device, wherein the output device is located in the defibrillator housing.

20. The CPR therapy system of claim 19, wherein the processor is located in the defibrillator housing.

* * * * *